(12) United States Patent
Kimura

(10) Patent No.: US 6,520,023 B2
(45) Date of Patent: Feb. 18, 2003

(54) LOAD DETECTION STRUCTURE FOR VEHICLE SEAT

(75) Inventor: Toshimitsu Kimura, Tokyo (JP)

(73) Assignee: Tachi-s Co., Ltd., Tokyo (JP)

( * ) Notice: Subject to any disclaimer, the term of this patent is extended or adjusted under 35 U.S.C. 154(b) by 0 days.

(21) Appl. No.: 09/986,091

(22) Filed: Nov. 7, 2001

(65) Prior Publication Data

US 2002/0062699 A1 May 30, 2002

(51) Int. Cl.[7] .................................................. G01N 3/00
(52) U.S. Cl. ........................................................ 73/795
(58) Field of Search ........................ 73/795, 782, 774, 73/781, 788, 789

(56) References Cited

FOREIGN PATENT DOCUMENTS

| JP | 11304579 | 10/1999 |
|---|---|---|
| JP | 11001153 | 4/2000 |

*Primary Examiner*—Harshad Patel
*Assistant Examiner*—Corey D. Mack
(74) *Attorney, Agent, or Firm*—Browdy and Neimark, P.L.L.C.

(57) ABSTRACT

A load detection structure in a vehicle seat with a support leg member, which includes a block member of rigid yet resilient recovery property and a strain gauge attached thereon. The block member is interposed between the seat and support leg member, such that a securing portion thereof is secured to the seat, whereas a pivotal end portion thereof is rotatably pivoted to the support leg member. The securing portion is displaced in a vertical direction due to a vertical load applied to the seat, while the pivotal end portion is rotated, so as to cause deflection in the block member, which is detected by the strain gauge. It may be so arranged that the block member is rotatable about its central axis, thereby being prevented against twist due to a lateral load applied to the seat. An auxiliary linkage is provided to insure preventing such twist of block member.

9 Claims, 4 Drawing Sheets

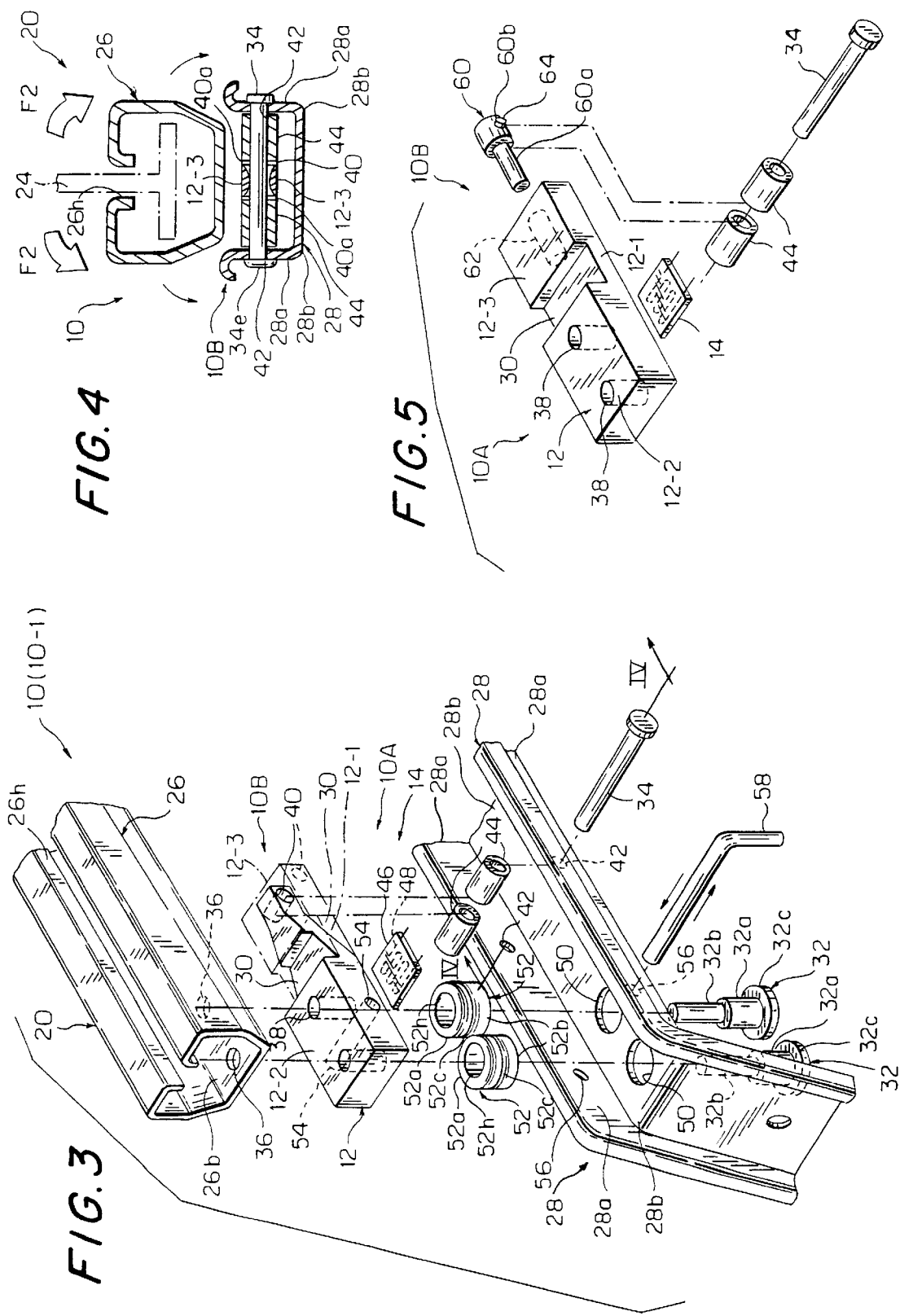

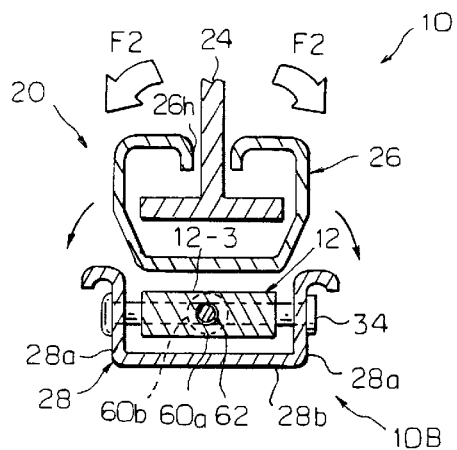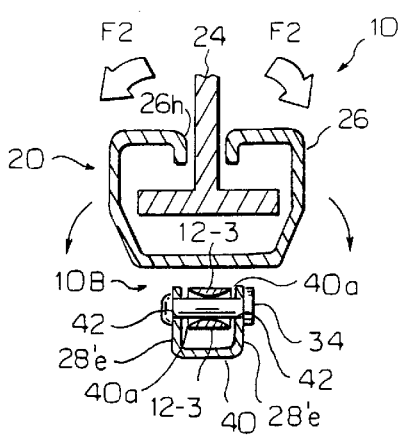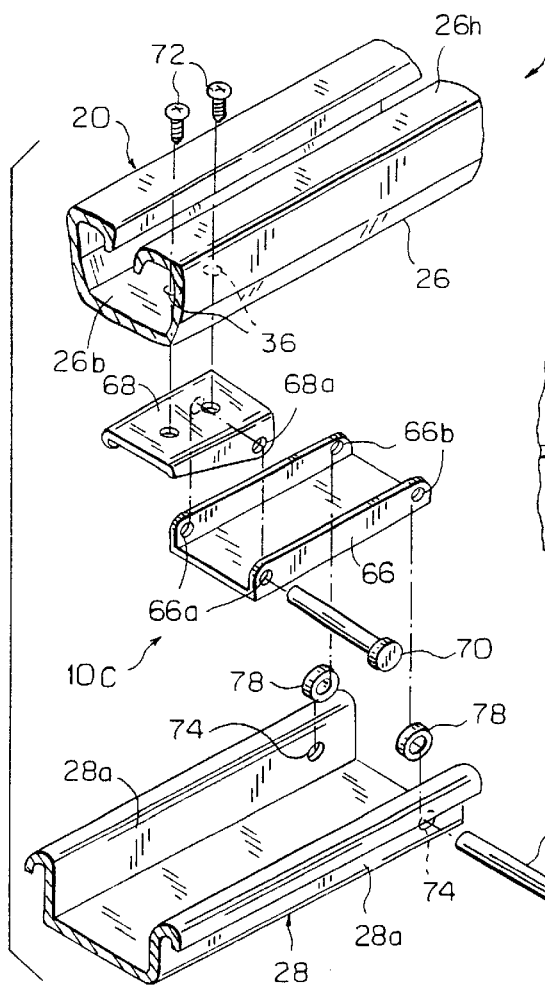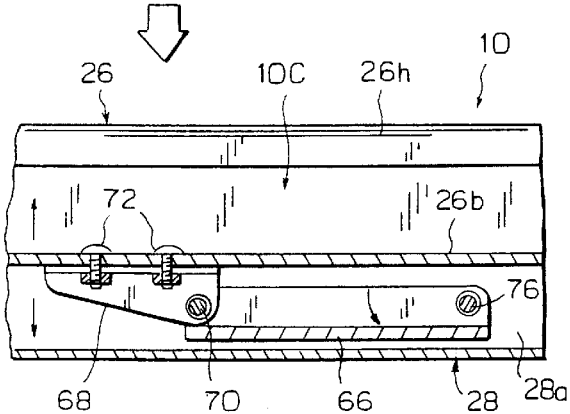

LOAD DETECTION STRUCTURE FOR VEHICLE SEAT

BACKGROUND OF INVENTION

1. Field of the Invention

The present invention relates to a structure allowing for detection of a load applied to a vehicle seat. In particular, the invention is directed to such load detection structure for use in a vehicle seat.

2. Description of Prior Art

Recent years have witnessed a tendency for various automatically controlled functions and mechanisms to be increasingly incorporated in vehicle or automobiles, including safety devices such as air bags for protecting passengers against a great impact automatically in response to a collision, as well as various kinds of seat position adjustment devices for automatically adjusting the positions of seat sensitive to driver's or passenger's physiques and seating conditions. With such automated control innovations, there have been also found technical improvements to a passenger detection system for detecting the presence and absence of a passenger or driver in a seat of vehicle in advance before actuating or stopping the associated mechanical elements to automatically control various functions and mechanisms built in the seat.

Normally, the passenger detection system employs various sensors (e.g. a pressure sensitive element) which detect the weight of a passenger on a seat and emit a signal to electronic control systems for automatic control of various mechanical elements related to the seat. Most of the sensors are of a simple structure which can only sense the presence and absence of passenger on a seat, but the recent high-tech control technology inevitably requires that the sensors should further detect whether the passenger is an adult or a child as with an air bag control system for instance.

To meet the demand, there have been proposed sensor systems for numerically detecting the weight of passenger or a corresponding load applied to the seat, determining whether the passenger is adult or child, according to a numerical data obtained, and then controlling and adjusting the associated mechanical elements to optimal conditions suited for the adult or child (e.g. controlling air bag), as disclosed from the Japanese Laid-Open Patent Publications Nos. 11-001153 and 11-304579. Namely, the Japanese Laid-Open Patent Publication No. 11-001153 shows a combination of an impact sensor and four load sensors, wherein each of the four load sensors is interposed between a slide rail device on which the seat is mounted and a support leg member fixed on the floor of vehicle. It also suggests an H-shaped base plate on which wiring of the load sensors is collectively arranged for electrical connection with another one cable. According thereto, the weight of an occupant on the seat is detected by the four load sensors in a collision case, and a signal emitted therefrom is determined by a control unit as to the numerical amount of the occupant's weight, so that the air bag is adjusted in inflation according to the numerical data on the occupant's weight, thereby realizing a proper inflation of air back to protect the occupant optimally according to his or her physique. On the other hand, the Japanese Laid-Open Patent Publication. No. 11-304579 discloses plural link mechanisms each having an arm pivoted therein, the link mechanisms being arranged between a slide rail fixed to a seat and a support base fixed on the floor of vehicle. In this prior art, a load sensor is provided at the free end portion of each arm of the link mechanism, such that a load applied vertically to the seat is imparted through the pivoted arm as an amplified or reduced vertical motion to the load sensor which then detects the amount of such vertical motion and determine a total weight of the seat and occupant on the seat. This reference states that a signal corresponding to the total weight may be emitted from the load sensors to a control unit associated with air bag and seat adjustment device, for instance.

However, the Japanese Laid-Open Patent Publication No. 11-001153 has no description regarding the mechanical structure of load sensor itself, and has no specific teaching on how the load sensor structurally supports the seat and how it actions to detect the seat occupant's weight. This prior art is therefore neither realistic nor practical in assembling an optimal mechanical structure between the sensor and seat. The Japanese Laid-Open Patent Publication No. 11-304579 is found defective in that its link mechanism and pivoted arm are complicated in structure and further they occupy much of space heightwise between the seat and slide rail device, which results in the seat becoming large vertically in size and increasing its weight. Consequently, there remains a room of improvement in materializing a simplified and effective structure for this sort of load detection system. Furthermore, as with those prior arts, most of conventional load detection structures are adapted to only detect a vertically applied load, which are not provided with any means for preventing a twisting deformation of the load sensors. For, such twisting deformation will occur when the seat is subjected to lateral inclination due to irregular vibration of vehicle running on a rough and curved road as well as the weight of seat occupant being excessively applied in one of the rightward and leftward directions relative to the seat. In that case, the load sensors can not precisely detect the amount of load and it is of a high likelihood that an air back or seat adjustment mechanism connected to the sensors will not be controlled well to cause an inconvenience and trouble to the seat occupant.

SUMMARY OF THE INVENTION

In view of the above-stated drawbacks, it is therefore a primary purpose of the present invention to provide an improved load detection structure which is greatly simplified in structure with reduced number of constituent elements and effective in avoiding undesired increase in height of the seat.

In order to achieve such purpose, according to the present invention, the load detection structure in combination with a vehicle seat having a seat cushion and a support leg means, includes a load detection means for detecting a load applied from a seat occupant to the vehicle seat, the load detection means comprising:

a block member having an elongated body extending in the longitudinal direction thereof, the block member having a rigid yet elastically deformable property and including, defined therein, a securing portion, a pivotal end portion, and a thin intermediate portion between the securing portion and pivot end portion, wherein the pivotal end portion has an upper side formed lower than an upper side of the securing portion, and the thin intermediate portion is defined by forming a recession in an upper side region of the block member in a direction transversely thereof at a point between the securing portion and pivotal end portion;

a strain gauge means fixedly attached to the thin intermediate portion of block member;

a vertically guiding and connecting means provided in the securing portion of block member, the support leg member, and a bottom side of seat cushion, the vertically guiding and connecting means being for securely connecting the securing portion of block member with a bottom side of the seat cushion and allowing vertical displacement of the securing portion between the bottom side of seat cushion and the support leg means; and the block member being interposed between the bottom side of seat cushion and the support leg means in such a manner that the securing portion of block member is securely connected with the bottom side of seat cushion via the vertically guiding and connecting means, whereas the pivotal end portion of block member is pivotally connected with the support leg means at a predetermined pivot point, wherein, when a downward load is applied to the seat in a vertical direction, the securing portion of block member is displaced in a generally rectilinear downward direction, while at the same time, the pivotal end portion of block member is rotated about the pivot point, whereupon a difference is caused in movement and direction between the securing portion and the pivotal end portion, which results in a deflection of the thin intermediate portion, and, in response thereto, the strain gauge detects an amount of the deflection and emits a corresponding value indicative of an amount of the load.

Accordingly, the block member is subjected to vertical deflection only within the height-wise range between the bottom side of seat cushion and support leg member. Thus, such heightwise thin construction does not lead to increase in height of the seat and it is possible to keep the seat situated at as low level as possible with reference to a vehicle floor. Furthermore, there is eliminated the need to provide a great number of intricate parts and fittings for assembling the load detection structure in the seat as found in the prior art.

In one aspect of the present invention, a twist prevention means may be provided in the pivotal end portion of block member, which twist prevention means allows the block member to be rotatable and inclinable about a central axis thereof in one of two symmetrical directions relative to a central line of the support leg member in response to a lateral load being applied to the seat in one of leftward and rightward directions intersecting the vertical direction of said downward load, to thereby prevent the thin intermediate portion of the block member from being twisted by the lateral load.

In another aspect of the invention, an auxiliary linkage means may be pivotally provided between the bottom side of seat cushion and the support leg means, which auxiliary linkage is so pivotally movable as to aid in only vertical movement of the seat cushion or the vehicle seat to and from the support leg means, thereby preventing the thin intermediate portion of block member from being twisted by the lateral load.

Other various features and advantages of the invention will become apparent from reading of the descriptions hereinafter, with reference to the annexed drawings.

BRIEF DESCRIPTION OF THE DRAWINGS

FIG. 3 is a partly broken, exploded schematic perspective view of the principal part of the load detection structure, which suggests providing one exemplary mode of a twist prevention means therein;

FIG. 4 is a sectional view taken along the line IV—IV in the FIG. 3;

FIG. 5 is another alternative mode of a block member usable in the load detection structure; structure;

FIG. 8 is a sectional view taken along the line VIII—VIII in the FIG. 6;

FIG. 9 is a sectional view taken along the line IX—IX in the FIG. 7;

FIG. 10 is a partly broken perspective view showing an auxiliary linkage means in the load detection structure; and FIG. 11 is a side view partly in section of the auxiliary linkage means.

DETAILED DESCRIPTION OF PREFERRED EMBODIMENT OF THE PRESENT INVENTION

Figure 1:
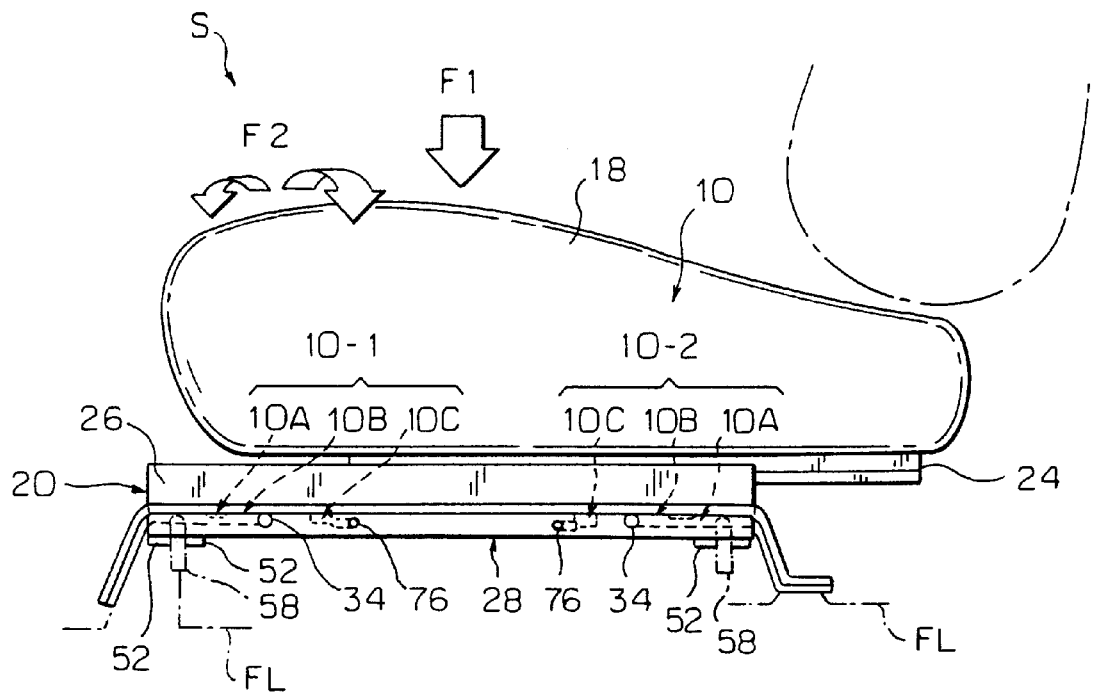
FIG. 1 is a partly broken schematic side view showing a principal part of a load detection structure in accordance with the present invention, which is applied to a vehicle seat.

Referring to FIGS. 1 through 12, there is illustrated one preferred mode of load detection structure applicable to a vehicle seat in accordance with the present invention. Reference is first made to FIG. 1 in which designations (10) each generally represents a load detection structure provided between a slide rail device (20) and a support leg member (28) in a novel simplified manner with various structural features, which is a main novel aspect of the present invention as will be described. Also, as will be elaborated later, as far as the illustrated embodiment is concerned, the load detection structure (10) may preferably be embodied by a load detection means (10A) for detecting an amount of vertically applied downward load (F1) (i.e. a weight of an occupant on a seat (S)); a twist prevention means (10B) for preventing the load detection means (10A) from being twisted by laterally applied load (F2) (i.e. a leftward or rightward applied load or force); and an auxiliary linkage means (10C) for aiding in precise detection of the load detection means (10A) with respect to the vertically applied downward load (F1). Of course, such combination of three means is not imitative, but it is optional to use one of them alone or two of them, depending on a required design.

As is known, the slide rail device (20) comprises a stationary lower rail (26) to be fixed on a floor (FL) of a vehicle (not shown) and a movable upper rail (24) slidably fitted in and along the lower rail (26). The typical configuration of such slide rail device (20) is shown in the figures, wherein the movable upper rail (24) has generally inverted-T-shaped base portion slidably accommodated within the lower rail (26) via steel balls and rollers (not shown). As seen from FIG. 1, the upper rail (24) is fixedly attached to a seat cushion (18) of a vehicle seat (S) whereas the lower rail (26) is securely and operatively attached via the load detection structure (10) upon the support leg member (28). Support leg member (28) is firmly fastened on the vehicle floor (FL). The details of this structure will be described later.

Though not shown clearly, in fact, both slide rail device (20) and support leg member (28) are each provided in pair. Namely, a pair of slide rail devices (20) are provided under the bottom of seat cushion (18) and a pair of support leg members (28) are provided for supportively receiving those two slide rail devices (20) thereon, respectively. Of course, the load detection structure (10), a principal part of the present invention, is interposed between each slide rail device (20) and each support leg member (28), and therefore a pair of load detection structures (10) are arranged under the seat (S).

According to the embodiment shown in FIG. 1, the load detection structure (10) is divided into forward and rearward load detection structures (10-1) (10-2) which are respectively disposed in the forward and rearward regions of a mutually mated pair of lower rail (26) and support leg member (28) Therefore, as far as the present embodiment is concerned, while not shown, it follows that a pair of forward load detection structures (10-1) are so arranged forwardly of the seat (S) that they are respectively disposed in the forward regions of left-side mated pair of lower rail (26) and support leg member (28) and in the forward regions of right-side mated pair of lower rail (26) and support leg member (28), whereas a pair of rearward load detection structures (10-2) are so arranged rearwardly of the seat (S) that they are respectively disposed in the rearward regions of right-side mated pair of lower rail (26) and support leg member (28) and in the rearward regions of left-side mated pair of lower rail (26) and support leg member (28). Since all the load detection structures (10-1) (10-2), the pair of slide rail devices (20) and the pair of support leg members (28) are identical in structure to one another, description will be made only of one forward load detection structure (10-1) in one of the two slide rail devices (20) and one of the two support leg members (28), for the sake of simplicity.

Within a generic concept of the present invention, the load detection means (10A) included in the load detection structure (10) is workable to detect an amount of a load (F1) applied vertically from an occupant on the seat (S) and embodied by:

(a) a block member (12) having a pivotal end portion (12-3), a vertically movable securing base portion (12-2) and a thin intermediate portion (12-1), wherein the securing base portion (12-2) is provided with a vertically guiding and securing means for not only securing that particular base portion (12-2) to the lower rail (26) or the seat (S) and but also guiding the same (12-2) vertically in a generally rectilinear direction between the seat (S) and the support leg member (28); and (b) a strain gauge (14) for detecting a deflection of the block member (12) which is caused by a difference in movement and direction between the pivotal rotation of the pivotally rotatable end portion (12-3) and the vertical displacement of the rectilinearly movable securing base portion (12-2).

According to the illustrated mode, in brief, the block member (12) is rotatably connected with the support leg member (28) at a given pivot point in the pivotal end portion (12-3) thereof (at 40 or 34 as will be described), while being connected at the securing base portion (12-2) thereof between the slide rail device (20) and support leg member (28), so that the thin intermediate portion (12-1) is deflectable in the vertical direction relative to that pivot point due to the afore-stated reasons. The aforementioned vertically guiding and securing means may be embodied, for example, by two securing pins (32) (32) and other peripheral elements which will be elaborated later, although it is not imitative.

As shown, the strain gauge (14) is attached tight (via an adhesive for example) on the bottom side of the block member thin intermediate portion (12-1) for detecting an amount of strain or deflection mentioned above, which is caused in the block member (12). The strain gauge (14) is of a known type comprising an electrical insulating thin plate (46) and a metallic resistance wire (48) embedded sinuously in that thin plate (46). Of course, the thin plate (46) is of an elastic property and may be resiliently deformable. The strain gauge (14) is not imitative, but may be formed in any otherwise manner without using such resistance wire (48) insofar as it can detect the deflection of block member (12).

Figure 2:
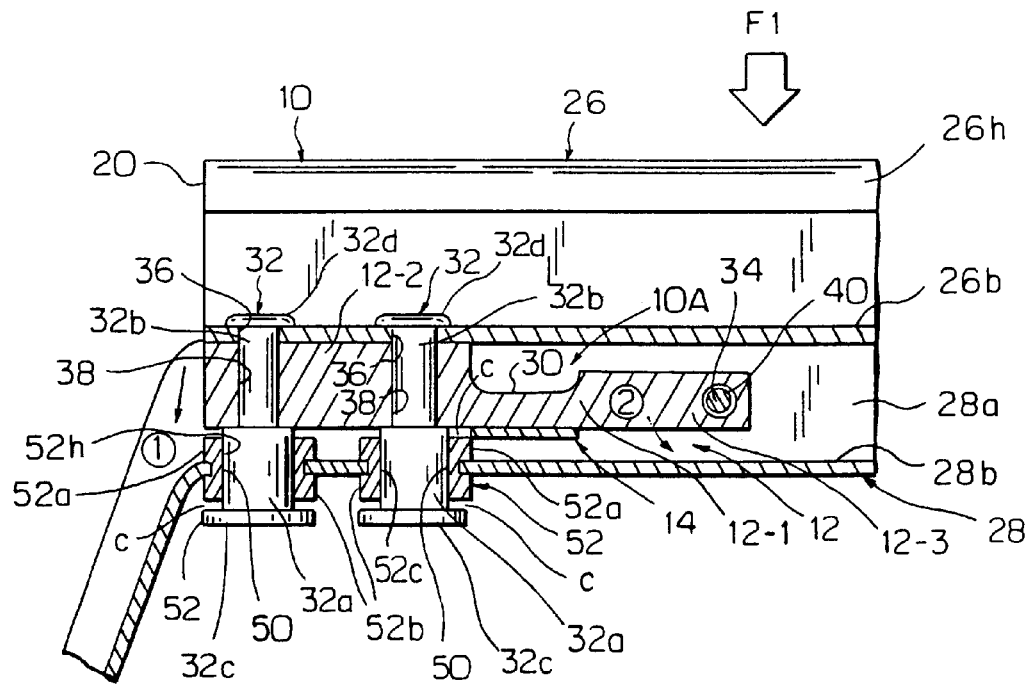
FIG. 2 is a partly broken sectional view showing a basic generic structure of a block member and other principal parts in the load detection structure, and explanatorily showing a deflection of the block member.

The block member (12) is generally of a longitudinally extending plate-like configuration which elongates its body lengthwise, thus having a body of large longitudinal length with a small width relative thereto, as seen from FIGS. 2 and 3. Also, it is formed from a rigid yet resiliently deformable material having a property that tends to recover into its original shape even when subjected to deformation by a great external load applied thereto. For that purpose, preferably, the block member (12) may be formed from a spring steel material. As best shown in FIGS. 2 and 3, the block member (12) is so formed to have, defined therein, a pivotal end portion (12-3), a securing base portion (12-2) which is relatively larger in heightwise thickness than the pivot end portion (12-3), and a thin intermediate portion (12-1) which is formed relatively thin heightwise between those two portions (12-2) (12-3). It is thus observed from FIG. 2 that the upper surface of the pivotal end portion (12-3) is lower than the upper surface of the securing base end portion (12-2), which allows the pivotal end portion (12-3) per se to rotate about the pivot point (at 40). The thin intermediate portion (12-1) is defined by forming a cutout region (30) in the corresponding upper half of intermediate area of block member (12) such that the cutout region (30) penetrates or extends transversely thereof. As will become apparent later, the thin intermediate portion (12-1) is a point giving a vertical resilient bendability of the block member (12) relative to the pivot point (at 40 or 34) of the end portion (12-3).

It is noted that the strain gauge (14) may be fixedly attached on the cutout region (30) of thin intermediate portion (12-1) by means of adhesive or the like.

In accordance with the generic mode of the load detection means (10) compassed by the present invention, the block member (12) is interposed between the lower rail (26) (i.e. the bottom side of seat (S)) and the support leg member (28) via the aforementioned vertically guiding and securing means and a pivot pin (34).

Reference is now made to FIG. 2 which shows a basic structural concept of the load detection means (10A) commonly applicable to all the illustrated embodiments in accordance with the present invention, which is intended to detect a vertically applied load (F1) imparted from an occupant on the seat (S). Now, a specific description will be made of such basic structural aspect of the load detection means (10A). As viewed mainly from this FIG. 2 partly in conjunction with FIG. 3, in general, the block member (12) is provided with the vertically guiding and securing means, as noted earlier, which specifically comprises: a pair of vertically extending securing through-bores (38) (38) formed vertically in and through the securing portion (12-2) thereof; a pair of securing pins (32) (32); a pair of securing holes (36) (36) formed in the bottom wall (26b) of lower rail (26); and a pair of holes (50) (50) formed in the base area (28b) of support leg member (28). The block member (12) is also formed with a horizontally extending bearing through-bore (40) in the pivotal end portion (12-3) thereof. The securing pin (32) is a rivet-type pin whose one end can be riveted. Each of the two securing pines (32) is so formed to have a circular flat head (32c), a large-diameter shank portion (32a) and a small-diameter shank portion (32b) defined integrally together, wherein the free end of the small-diameter shank portion (32b) can be riveted. On the other hand, perforated in the bottom wall (26b) of lower rail (26) are the two securing holes (36) (36) such as to be in a concentric alignment with the respective two securing through-bores (38) (38) of block member (12). Also, perforated in the base area (28b) of support leg member (28) are the two holes (50) (50) such as to be in a concentric alignment with the respective two securing through-bores (38) (38). With regard to the pivot pin (34), it is a normal rivet-type pin having a shank of a certain length and a circular flat head, as illustrated. In this connection, a pair of bearing holes (42) (42), through which the pin (34) is to pass, are respectively formed in a pair of vertical walls (28a) (28a) of support leg member (28) in a mutually opposed relation.

It is noted that both diameters of the securing through-bores (38) and securing holes (36) are generally equal to or slightly larger than the external diameter of the small-diameter shank portion (32b) of securing pin (32), and that the diameter of each hole (50) is larger than the external diameter of the larger-diameter shank portion (32a) of securing pin (32), but smaller than the external diameter of the flat head (32c) of the same pin (32).

In assembly, at first, by passing the pivot pin (34) through both bearing holes (42) and bearing through-bore (40) and riveting the free end of pin (34) (as shown at (34e) in FIG. 4), the pivotal end portion (12-3) of block member (12) is rotatably coupled with the support leg member (28). At this point, the whole body of block member (12) is fitted and received in a space of generally channel cross-section defined by the two vertical walls (28a) and base area (28b) of support leg member (28). In other words, the two lateral walls of the block member (12) are substantially in a slidable contact with the two vertical walls (28a) of support leg member (28), respectively, so that the support leg member (28) per se is prevented against transversal movement with respect to the support leg member (28). Then, the two securing pins (32) are respectively passed through the two holes (50), the two through-bores (38) and the two holes (36) until the shoulders of the large-diameter portions (32a) of two securing pins (32) are abutted against the bottom surface of block member (12). Finally, both ends of small-diameter shank portion (32b) of securing pins (32) are riveted, as at (32d) in FIG. 2, to thereby firmly fasten the base securing portion (12-2) of block member (12) to the bottom wall (26b) of lower rail (26). In this regard, it is observed from FIG. 2 that each large-diameter shank portion (32a) of securing pin (32) extends downwardly through the corresponding hole (50), with a small clearance given peripherally thereof to thereby space the large-diameter shank portion (32a) from the surrounding circular edge of the hole (50), and that each large-diameter shank portion (32a) terminates in the circular flat head (32c) which is situated at a predetermined level below the base area (28b) of support leg member (28).

It is noted here that, in accordance with the vertically guiding and securing means, instead of the two securing pins (32), two integral projections equivalent to the pins (32) may be formed integrally in the block member base securing portion (12-2). Namely, while not shown, two columnar projections each with a circular flat head, which are each equivalent in size and function to the larger-diameter shank portion (32a) and circular flat head (32c) of securing pin (32), may be integrally formed on the bottom surface of the block member securing portion (12-2). Also, another two columnar projections, each being equivalent in size to the end portion of the small-diameter shank portion (32b) of securing pin (32), may be integraly formed on the upper surface of the block member base securing portion (12-2).

Designations (52) (52) denote a pair of elastic ring elements having an elastically deformable property, each being adapted to elastically embrace the large-diameter shank portion (32a) of securing pin (32) and fill the foregoing space between that particular shank portion (32a) and the circular edge of hole (50). Each elastic ring element (52) is so formed to have an upper half portion (52a), a lower half portion (52b), an annular groove (52c) defined between the upper and lower half portions (52a) (52b), the annular groove (52c) being adapted to elastically engage the whole circular edge of hole (50), and a through-hole (52h) penetrating vertically through the body of element (52), the through-hole (52h) being to be elastically attached about the large-diameter portion (32a) of securing pin (32). Accordingly, as shown in FIG. 2, the two large-diameter portions (32a) are elastically supported within the respective two holes (50) via the respective two ring elements (52). Preferably, the ring element (52) may be formed from a synthetic rubber material or a suitable rubber substitute. But, this is not imitative. Other elastic means, such as a spring element, be used insofar as it serves the same function as the ring element (52) stated above.

In this regard, as in the FIG. 2, it is important that a certain clearance (C) be provided not only between the upper end of ring element (52) and the bottom wall of block member (12), but also between the lower end of ring element (52) and the flat head (32c) of securing pin (32). For, that clearance (C) allows a minimum required degree of vertical elastic deflection of the block member (12) (which will be described later) without interference with the ring element (52) and thus allows such required vertical deflection to be precisely detected by the strain gauge (14). The provision of those two elastic ring elements (52) is effective in elastically limiting unnecessary vertical deflection of block member (12), thereby reducing vertical wabbling or vibration of the seat (S) to a smallest possible degree, while protecting the block member (12) against damage due to its collision with the base area (28b) of support leg member (28). Also, this provision of elastic ring elements (52) retains both large-diameter shank portions (32a) and block member (12) in a condition out of direct contact with the support leg member base area (28b), thereby avoiding any objectionable noise which might be generated due to such direct contact. Further, the securing pin flat head (32c) and elastic ring element (52) cooperate with each other to serve as a stopper for positively preventing upward separation of the lower rail (26) from the support leg member (28) when an excessive upward force is exerted on the slide rail device (20), attempting to pull the same in the upward direction.

With the above-described basic construction of the load detection means (10A), it can be seen from FIGS. 1 and 2 that, when a vertical load or a weight of occupant on the seat (S), as designated by (F1), is applied to the slide rail device (20), the corresponding downward force is directly imparted to the securing base portion (12-2) of block member (12), thus causing downward displacement of that particular securing base portion (12-2) as indicated by the arrow ① and, concurrent therewith, the pivotal end portion (12-3) of the same block member (12) is caused by such downward displacement to rotate downwardly as indicated the arrow ② relative to the pivot pin (34). As a result thereof, a deflection is caused in the thin intermediate portion (12-1) of block member (12), in response to which, the strain gauge (14) immediately detects an amount of such deflection, determines it as a weight of the occupant on the seat (S), and emits a corresponding electric signal to a control unit (not shown).

In accordance with the present invention, as mentioned earlier, the load detection structure (10) may also include a twist prevention means (10B) and an auxiliary linkage means (10C). As shown in FIG. 1, it is of a high likelihood that the laterally applied or leftward-rightward applied load (F2) will be exerted on the seat (S) in addition to the vertically downward load (F1), due to an irregular vibration or turning of a vehicle (not shown) in which the seat (S) is provided, when the vehicle runs on a rough and curved road. In that case, such lateral load (F2) forcibly causes the lower rail (26) to incline in leftward or rightward direction with respect to the support leg member (28), with the result that the block member (12) is subjected to twist deformation, causing an error in detection of strain gauge (14) for the vertically applied downward load (F1). In order to avoid such twist deformation and detection error, there may be added the twist prevention means (10B) in the present load detection structure. Twist prevention means (10B) allows the block member (12) to be rotatable and inclinable about a central axis thereof in one of two symmetrical directions relative to a central line of the support leg member (28) in response to the lateral load (F2) being applied to the seat (S) in one of the corresponding leftward and rightward directions intersecting the vertical direction of the downward load (F1), thereby insuring to prevent the thin intermediate portion (12-1) of block member (12) from being twisted by the lateral load (F2).

As one exemplary mode of the twist prevention means (10B), as indicated by one-dot chain line in FIG. 3, both thin intermediate and pivotal end portions (12-1) (12-3) of block member (12) may be cut formed into a tapered configuration as shown in the solid line in the FIG. 3, so that the pivotal end portion (12-1) becomes reduced in its widthwise thickness towards the central axis of block member (12) as it proceeds to the foremost end thereof. In that instance, there is greatly reduced a contact area between the bearing through-bore (40) and the pivot pin (34) so as to reduce an amount of interference of the pivot pin (34) with the leftward and rightward rotative inclination of the block member (12) relative to the central axis of that particular block member (12).

More preferably, as best shown in FIG. 4, the bearing through-hole (40) may be formed to have a pair of outwardly divergent bore portions (40a) (40a) defined therein so as to not only substantially provide a point contact area between the through-bore (40) and pivot pin (34), but also create a certain play about the pivot pin (34) on the opposite sides of such point contact area, thereby insuring to allow the block member (12) to be inclinable in the leftward and rightward directions relative to the central axis thereof. Therefore, upon a lateral load (F2) being applied to both slide rail device (20) and block member (12) in one of the leftward and rightward directions, the block member (12) is immediately rotated and inclined about the foregoing substantial point contact area in the corresponding one of the leftward and rightward directions, whereby the whole body of block member (12) is protected against twist deformation, thus allowing its thin intermediate portion (12-1) to be deflected only in the vertical direction, so that the strain gauge (14) can only detect an amount of the vertically applied downward load (F1) in a precise manner. In the present mode, a pair of tubular spacers (44) are so attached about the pivot pin (34) as to be disposed on the opposite sides of the block member lend portion (12-3) to prevent undesired lateral dislocation or movement of the block member (12).

Figures 6, 7:
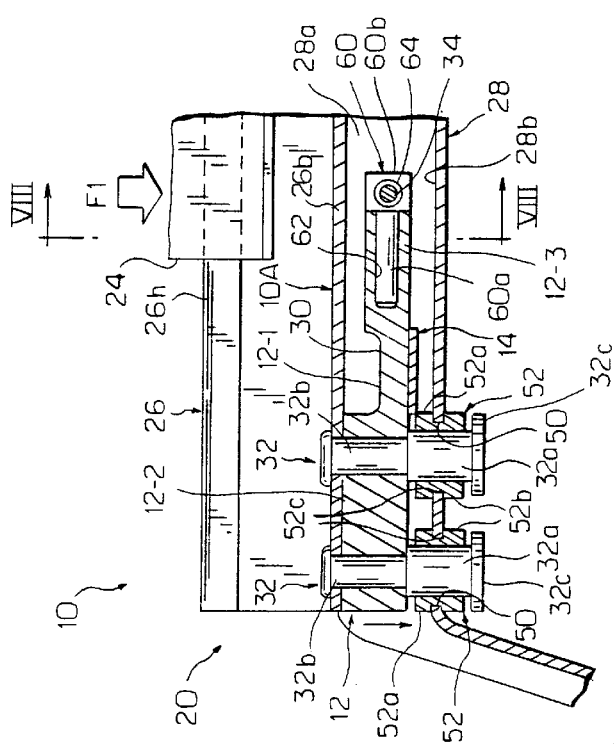
FIG. 6 is a partly broken sectional view showing a principal part of the load detection structure provided with another exemplary mode of a twist prevention means.
FIG. 7 is a partly broken schematic perspective view of the load detection structure in which another alternative mode of support leg member is provided.

In another alternative exemplary mode of the twist prevention means (10B), as suggested in FIG. 5, the original (non-cut) pivotal end portion (12-3) of block member (12) may be used, in which a longitudinal bearing bore (62) is formed, extending in the longitudinal direction thereof, instead of forming the afore-stated transversely extending bearing bore (40) therein. As shown, the longitudinal bearing bore (62) extends along the central longitudinal line of the block member (12). In this mode, a joint pin (60) may be used, which has a shank portion (60a) generally equal in length to the afore-said bearing bore (62), a head (60b) large in diameter relative to the shank portion (60a), and a transversely extending bearing through-bore (64) formed in the head (60b). As best seen from the FIG. 6, the shank portion (60a) of joint pin (60) is rotatably fit in the bearing bore (62) of block member (12), while the head (60b) is only exposed externally of the block member (12). Needless to mention, in this embodiment, all the constitute members described above (e.g. the lower rail (26), the support leg member (28), two elastic ring elements (52), two securing pins (32) and so forth) are used, and therefore, repetition of description thereon is omitted. In assembly, as understandable from FIGS. 5 and 6 partly in conjunction with FIG. 3, the pivot pin (34) are inserted through the hole (42) of support leg member (28) and the transverse bearing through-bore (64) via the two spacers (44), with the free end of the pivot pin (34) riveted, and then, as likewise in the foregoing first mode shown in FIG. 3, the two securing pines (32) are inserted through the two respective holes (50) of support leg member (28), the two respective elastic ring elements (52), the two respective securing through-bores (38) of block member (12) and finally the two respective securing holes (36) of lower rail (26). Of course, both small-diameter shank portions (32b) of two securing pins (32) are riveted at their respective ends to firmly secure the block member (12) to the lower rail (26), while both large-diameter shank portions (32a) are situated within the two respective holes (50) via the two respective elastic ring elements (52), as shown in FIG. 6. Excepting the twist prevention means (10B), all structure and constituent members used in this particular mode are identical to those of the first embodiment described above and shown in FIG. 3, and therefore, repetition of description on the corresponding members and elements is omitted for the sake of simplicity. It is appreciated that, in the present second mode, the block member (12) itself is rotatable about the axis of joint pin (60); in other words, the block member (12) is free to rotate about its central axis, and therefore, as shown in FIG. 8, upon a leftward or rightward load (F2) being applied to both slide rail device (20) and block member (12), the block member (12) is immediately inclined relative to the central axis thereof in the corresponding leftward or rightward direction, whereby the thin intermediate portion (12-1) of block member (12) is prevented against twist deformation and thus, the strain gauge (14) can only detect an amount of the vertically applied load (F1) in a precise manner.

It is however noted that the above-described two modes of the twist prevention means (10B) are just exemplary and non-distinctive modes because they are equivalent to each other only in terms of preventing the block member (12) against twist deformation due to the lateral load (F2), and therefore, the twist prevention means (10B) per se may be embodied in any other ways possible within the gist, purposes and scopes of the present invention.

FIG. 7 shows an example where there may be provided another mode of support leg member (28') having a narrow end portion at (28'), which is suited to support the aforementioned tapered end portion (12-2) of block member (12). As shown, such narrow end portion comprises a pair of spaced-apart lugs (28'e) (28'e), each being formed with a securing hole (42). In this mode, a pivot pin (34) of a relatively short length may be inserted through the holes (42) and through-bore (40) of block member (12), without the two tubular spaces (44), so that the pivotal end portion (12-3) of block member (12) is rotatably connected with the support leg member (28). FIG. 9 shows the leftward and rightward inclinability of the block member tapered end portion (12-3) on the two support lugs (28'e), as indicated by the leftward and rightward arrows, in response to the lateral load (F2), thereby preventing twist deformation of the block member thin intermediate portion (12-1). This twist prevention effect is just the same as described in the first embodiment shown in FIGS. 3 and 4, and any further elaboration thereon is deleted.

Referring to FIG. 10 and 11, there is shown one exemplary mode of auxiliary linkage means (10C) which may be provided as a part of the load detection structure (10) in accordance with the present invention. As illustrated, the auxiliary linkage means (10C) may be comprised of a connecting bracket (68) of generally inverted-U-shaped cross-section and a movable link (66) of generally U-shaped cross-section. As can be seen from FIG. 10, the connecting bracket (68) is fastened by two securing screws (72) via two holes (68a) to the bottom wall (26b) of lower rail (26). On the other hand, the movable link (66) is pivotally connected at its two forward holes (66a) with the respective two holes (68a) of bracket (68) via a first pin (70). The movable link (66) is also pivotally connected at its two rearward holes (66b), via a second pin (76) and two spacers (78), with the respective two holes (74) which are formed in the two vertical walls (28a) of support leg member (28), respectively. With this linkage structure, the lower rail (26) or slide rail device (20) is only guided in the vertical direction, as indicated by the upward and downward arrows in FIG. 11, and thus positively prevented against twist deformation and dislocation in the lateral direction with respect to the support leg member (28). That is, as understandable from FIG. 11, upon a vertical downward load (F1) (i.e. a weight of seat occupant) being exerted upon the lower rail (26), the link (66) is simultaneously rotated downwardly relative to the second pin (76) to guide the lower rail (26) in the downward direction only. Hence, the block member base securing portion (12-2) fixed to the lower rail (26) is subjected to vertical deflection only, not subjected to any twist deformation due to the above-stated lateral load (F2). This insures that the strain gauge (14) precisely detects the deflection of block member intermediate portion (12-1) as a weight of an occupant on the seat (S), in addition to the foregoing twist prevention means (10B).

Designation (58) stands for a locating pin that may preferably be used to provisionally locate and retain both support leg member (28) and block member (12) at a predetermined point relative to the lower rail (26) or the seat cushion (18) so that the support leg member (28) is temporarily prevented against dislocation and rotation relative to the lower rail (26) or the seat cushion (18). This effectively allows the seat (S) with the present load detection structure (10) to be precisely and easily fastened to a predetermined point in the floor of vehicle (FL). More specifically, for instance, reference is first made to FIG. 3. In this mode, a pair of locating holes (56) are respectively formed in the two vertical walls (28a) of long support leg member (28) as shown, and also, a locating through-bore (54) is formed in the securing base portion (12-2) of block member (12) in the transverse direction thereof such as to extend between the two vertically extending through-bores (38). Prior to fastening the support leg member (28) to the floor (FL), the locating pin (58) is inserted through all the holes (56) and through-bore (54) to provisionally retain the support leg member (28) against any movement relative to the seat (S). Then, after having fastened the support leg member (28) (and the seat (S)) to the floor (FL), the locating pin (58) is drawn out of all those holes (56) and through-bore (54) to set the load detection means (10) in an active or deflectable state for detecting the load (F1). Reference is further made to FIG. 7 which shows the tapered mode of support leg member (28') stated previously. In that mode also, the same locating pin (58) as in FIG. 3 may be used for the same purpose of allowing the seat (S) to be precisely fastened to a predetermined point in the floor (F). Of course, the same locating holes (56) and locating through-bore (54) as in FIG. 3 may be formed in the support leg member vertical walls (28a) and the block member base securing portion (12-2), respectively. The process for using the locating pin (58) in the present mode of FIG. 7 is just the same as in the foregoing process described with reference to FIG. 3, and therefore, any further description thereon is omitted. Form the descriptions made thus far, it is appreciated that the present invention has the following effects and advantages:

(i) Basically, the load detection structure (10) is interposed between the slide rail device (20) and the support leg member (28) in a simplified pivoted manner. Namely, the longitudinally extending body of block member (12) with the strain gauge (14) attached thereto is pivotally connected with the support leg member (28) and secured to the lower rail (26) via the vertically guiding and securing means (e.g. at 32, 36, 38 and 50), such that, when a load (F1) is applied to the block member (12), the block member base securing portion (12-2) is subjected to a generally rectilinear movement, whereas by contrast, the block member end portion (12-3) subjected to a rotational movement. Thus, such difference in movement and direction results in a downward deflection of the block member thin intermediate portion (12-1), in response to which, the strain gauge (14) detects a degree of the deflection and emits an electric signal indicative of a weight of a seat occupant corresponding thereto. With such simplified arrangement, the block member (12) is subjected to vertical deflection only within the height-wise range between the support leg member (28) and lower rail (26). The auxiliary linkage means (10C) is also pivotally interposed and connected between the support leg member (28) and lower rail (26). Thus, it is appreciated that such heightwise thin construction does not lead to increase in height of the seat (S) and it is possible to keep the seat (S) situated at as low level as possible with reference to the floor. Furthermore, there is eliminated the need to provide a great number of intricate parts and fittings for assembling the load detection structure (10) in the seat as found in the prior art. It is therefore quite easy for a worker to assemble the seat with such load detection structure (10) at highly reduced costs, and also, the worker can quickly secure the thus-assembled seat to the vehicle floor (F).

(ii) The load detection structure (10) includes a twist prevention means (10B) which is also defined along the longitudinal direction of the block member (12) as understandable from the illustrated embodiments (as shown in FIGS. 3 to 6 for instance) and thus does not interfere with the vertical deflection of the block member (12) within the heightwise range between the lower rail (26) and support leg member (28). With the twist prevention means (10B), the block member thin intermediate portion (12-1) is protected against twist deformation to enable the strain gauge (14) to only detect the vertical deflection of that particular portion (12-1) without any detection error caused from such twist deformation. In other words, the twist prevention means (10B) allows leftward and rightward inclination of the block member (12) about its central longitudinal axis when a lateral load is applied to the seat (S) in the corresponding leftward and rightward directions. As suggested in FIGS. 3 and 4, the twist prevention means (10B) may be embodied by tapering the block member pivotal end portion (12-3) towards the central axis thereof to thereby establishing a substantially point contact between the pivotal end portion (12-3) of block member (12) and the pivot pin (34) so as to allow the leftward and rightward inclination of the block member (12) itself about the central axis thereof. Or, alternatively, as suggested in FIGS. 5 and 6, the twist prevention means (10B) be embodied by providing the combination of bore (62) and joint pin (60) in the block member pivot end portion (12-3) along the central axis thereof so as to allow the leftward and rightward inclination of block member (12) itself about the central axis thereof. In any case, upon receiving a leftward or rightward lateral force (F2), the block member (12) per se is rotated about its central axis in the corresponding leftward or rightward direction, thereby preventing itself against twist deformation to insure a precise detection by the strain gauge (14) only of the vertical deflection of block member (12) to determine a weight of occupant on the seat (S).

(iii) Generally stated, it can be seen that the block member (12) has two downward projections, like the two large-diameter shank portions (32a), which are each dependent therefrom, passing through the respective two holes (50), such that a space is given between each of the two downward projections and each of the two holes (50), and that each of the two projections terminates in a circular flat head, like the head (32c), which is larger in diameter than each hole (50). Accordingly, when a great upward force is applied to the block member (12) through the slide rail device (20), attempting to separate the lower rail (26) from the support leg member (28), both circular flat heads (e.g. at 32c) of two projections (e.g. at 32a) are quickly brought upwardly to contact with the peripheral edge regions of two holes (50), which effectively prevents separation of the lower rail (26) from the support leg member (28). Further, an elastic element (52) may be filled between the downward projection (e.g. at 32a) and the hole (50) in a sense to limit an excessive vertical movement of the seat (S) with respect to the support leg member (28) as well as to avoid unpleasant or objectionable noise that might be generated from a direct contact between the projection and hole.

(iv) In addition to the twist prevention means (10B), the auxiliary linkage means (10C) also acts to protect the block member (12) against twist deformation due to the lateral load (F2) by restricting the displacement of lower rail (26) only to a vertical direction to and away from the support leg member (28). This insures that the strain gauge (14) precisely detects the vertical deflection of block member thin intermediate portion (12-1).

Finally, it should be understood that the present invention is not limited to the illustrated embodiment, but any other modifications, replacements and additions may be structurally applied thereto without departing from the scopes of the appended claims. For example, the load detection structure (10) may be interposed between the seat (S) and the support leg member (28), without using the slide rail device (20), by directly fastening the block member securing portion (12-2) to the bottom of seat (S). The twist prevention means (10B) may be provided only in the forward load detection structure (10-1) which is remote from the main seating point where a seat occupant's buttocks portion deeply rests in the seat (S) (adjacent to the rearward load detection structure (10-2)), if it is better to prevent the seat occupant from feeling a frequent inclination due to the twist prevention means (10B). Further, the present invention may also be applied to any other protection device than air bag and seat adjustment devices, as well as to various kinds of seats usable in a train, aircraft or vessel.

What is claimed is:

1. A load detection structure in combination with a vehicle seat including a seat cushion and a support leg means for supporting the vehicle seat, said load detection structure being disposed below the seat cushion and including a load detection means for detecting a load applied from an occupant on the vehicle seat, wherein said load detection means comprises:

a block member having an elongated body extending in the longitudinal direction thereof, said block member having a rigid yet elastically deformable property and including, defined therein, a securing portion, a pivotal end portion, and a thin intermediate portion between said securing portion and said pivotal end portion, wherein said pivotal end portion has an upper side lower than an upper side of said securing portion, and said thin intermediate portion is defined by forming a recession in an upper side region of the block member in a direction transversely thereof at a point between said securing portion and said pivotal end portion;

a strain gauge means fixedly attached to said thin intermediate portion of said block member;

a vertically guiding and connecting means provided in said securing portion of the block member, said support leg means and said bottom side of the seat cushion, said vertically guiding and connecting means being for securely connecting said securing portion of the block member with a bottom side of said seat cushion and guiding said securing portion in a vertical direction so that the securing portion is displaceable vertically in a generally rectilinear direction between said bottom side of the seat cushion and said support leg means; and said block member being interposed between said bottom side of the seat cushion and said support leg means in such a manner that said securing portion of the block member is securely connected with said bottom side of the seat cushion by said vertically guiding and connecting means, whereas said pivotal end portion of the block member is pivotally connected with said support leg means at a predetermined pivot point, wherein, when a downward load is applied to the seat in a vertical direction, said securing portion of the block member is displaced in a generally rectilinear downward direction, while at the same time, said pivotal end portion of the block member is rotated about said predetermined pivot point, whereupon a difference is caused in movement and direction between said securing portion and said pivotal end portion, thereby causing a deflection of said thin intermediate portion, and, in response thereto, said strain gauge detects an amount of said deflection and emits a corresponding value indicative of an amount of said load.

2. The load detection structure as defined in claim 1, wherein a slide rail device is fixedly provided on said bottom side of the seat cushion, and wherein said block member is interposed between said bottom side of the seat cushion and said support leg means in such a manner that the securing portion of the block member is securely connected with said slide rail device by said vertically guiding and connecting means, whereas said pivotal end portion of the block member is pivotally connected with said support leg means at said predetermined pivot point.

3. The load detection structure as defined in claim 1, wherein said vertically guiding and connecting means comprises: a projection means provided in said securing portion of the block member; and at least one hole formed in said support leg means, wherein said projection means has a first end portion securely connected with said bottom side of the seat and a second end portion extending downwardly through said at least one hole, with a small clearance given peripherally thereof to space the second end portion from said at least one hole, and wherein said second end portion of said projection means has a flat head larger in diameter than said at least one hole, with such an arrangement that said flat head is normally positioned at a level below and apart from said support leg means and is to be brought to contact therewith when an upward load is applied to said block member, thereby preventing separation of said block member from the support leg means.

4. The load detection structure according to claim 3, wherein said projection means comprises a securing pin provided in said securing portion of the block member, wherein said securing pin has a first end portion equivalent to said first end portion of the projection means and a second end portion equivalent to said second end portion of the projection means, wherein said second end portion of the securing pin extends downwardly through said at least one hole, with a small clearance given peripherally thereof to space the second end portion from said at least one hole, and wherein said second end portion of the securing pin has a flat head larger in diameter than said at least one hole, with such an arrangement that said flat head associated with the securing pin is normally positioned at a level below and apart from said support leg means and is to be brought to contact therewith when an upward load is applied to said block member, thereby preventing separation of said block member from the support leg means.

5. The load detection structure according to claim 3, wherein an elastic means is provided in said small clearance between said at least one hole and said second end portion of said projection means, said elastic means having: an upper half elastic portion disposed between said bottom side of the seat and said support leg means; and a lower half elastic portion disposed between said support leg means and said flat head of the projection means.

6. The load detection structure according to claim 4, wherein an elastic means is provided in said small clearance between said at least one hole and said second end portion of said securing pin, said elastic means having: an upper half elastic portion disposed between said bottom side of the seat and said support leg means; and a lower half elastic portion disposed between said support leg means and said flat head of said securing pin.

7. The load detection structure as defined in claim 1, which further comprises a twist prevention means provided in said pivotal end portion of said block member, said twist prevention means allowing said block member to be rotatable and inclinable about a central axis thereof in one of two symmetrical directions relative to a central line of said support leg means in response to a lateral load being applied to the seat in one of leftward and rightward directions intersecting the vertical direction of said downward load, to thereby prevent said thin intermediate portion of the block member from being twisted by said lateral load.

8. The load detection structure as defined in claim 1, which further comprises an auxiliary linkage means pivotally provided between said bottom side of the seat cushion and said support leg member, said auxiliary linkage means being so pivotally movable as to cause displacement of the seat cushion or the seat in a vertical direction to and from said support leg means, thereby serving to prevent said thin intermediate portion of the block member from being twisted by said lateral load.

9. The load detection structure as defined in claim 1, wherein a locating means is provided in said support leg means and said block member to provisionally retain said block member against any movement relative to said slide rail device, to thereby insure precise connection of both said block member and support leg means with the bottom side of the seat back, wherein said locating means comprises a locating pin; a pair of locating holes formed in said support leg means; and a pair of locating through-bores formed in said block member, and wherein insertion of said locating pin through said pair of locating holes and said pair of locating through-bores retains said block member provisionally against any movement and allows said precise connection.

* * * * *